(12) United States Patent
Sheplak et al.

(10) Patent No.: US 6,966,231 B2
(45) Date of Patent: Nov. 22, 2005

(54) MICROELECTROMECHANICAL FLOATING ELEMENT FLOW SENSOR

(75) Inventors: Mark Sheplak, Gainesville, FL (US); Louis N. Cattafesta, III, Gainesville, FL (US); Toshikazu Nishida, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 162 days.

(21) Appl. No.: 10/701,744

(22) Filed: Nov. 4, 2003

(65) Prior Publication Data
US 2005/0092106 A1    May 5, 2005

(51) Int. Cl.$^7$ ................................................ G01F 1/00
(52) U.S. Cl. ............................................... 73/861
(58) Field of Search ............................ 73/861, 862.623, 73/861.57

(56) References Cited

U.S. PATENT DOCUMENTS 5,404,755 A * 4/1995 Olson et al. .................. 73/639

OTHER PUBLICATIONS

Alfredsson et al., "The fluctuating wall-shear stress and the velocity field in the viscous sublayer," Phys. Fluids, 31:1026-1033,1988.
Akbar et al., "A Fully Integrated Temperature Compensation Technique for Piezoresistive Pressure Sensors," IEEE Transactions on Instrumentation and Measurement, 42:771-775, 1993.
Appukuttan et al., "Mixed Convection Induced by MEMS-Based Thermal Shear Stress Sensors," Numerical Heat Transfer Part A, 43:283-305, 2003, Copyright 2003 Taylor & Francis.
Arnold et al., "A Piezoresistive Microphone for Aeroacoustic Measurements," 2001 ASME International Mechanical Engineering Congress and Exposition, Nov. 11-16, 2001, New York, NY.
Arnold et al., "A directional acoustic array using silicon micromachined piezoresistive microphones," J. Acoust. Soc. Am., 113:289-298, 2003.
Bhardwaj et al., "S/N Optimization and Noise Considerations for Piezoresistive Microphones," Paper submitted to World Scientific on Jan. 29, 2004.

(Continued)

Primary Examiner—Edward Lefkowitz
Assistant Examiner—Jewel V. Thompson
(74) Attorney, Agent, or Firm—Akerman Senterfitt; Gregory A. Nelson; Michael K. Dixon

(57) ABSTRACT

An electromechanical floating element shear-stress sensor, which may also be referred to as a flow rate sensor, having one or more transduction mechanisms coupled to a support arm of a floating element wafer such that the transduction mechanisms are normal to the force applied to a top surface of the floating element. The transduction mechanisms may be generally attached to a side surface of one or more arms supporting the floating element and may be coupled together and to a processor using one or more contacts extending from the backside of the floating element sensor. Thus, the floating element shear-stress sensor may have an unobstructed surface past which a fluid may flow. The floating element may also include a temperature sensing system for accounting for affects of temperature on the floating element system.

37 Claims, 3 Drawing Sheets

OTHER PUBLICATIONS

Cain et al., "Development of a Wafer-Bonded, Silicon-Nitride Membrane Thermal Shear-Stress Sensor with Platinum Sensing Element, " Solid-State Sensor and Actuator Workshop, Hilton Head Island, SC. Jun. 4-8, 2000.

Cattafesta III et al., "Three-Dimensional Boundary-layer Transistion on a Swept Wing at Mach 3.5," AIAA Journal, 33:2032-2037, 1995.

Chandrasekaran et al., "Dynamic Calibration Technique for Thermal Shear Stress Sensors with Variable Mean Flow," 38th Aerospace Sciences Meeting & Exhibit, Reno, NV, Jan. 10-13, 2000.

Chandrasekaran et al., "Thermoelastically Actuated Acoustic Proximity Sensor with Integrated Through-Wafer Interconnects," Solid-State Sensor. Actuator and Microsystems Workshop, Hilton Head Island, SC, Jun. 2-6, 2002.

Cheng et al., "Electrical Through-Wafer Interconnects with Sub-PicoFarad Parasitic Capacitance," 2002.

Chow et al., "Process Compatible Polysilicon-Based Electrical Through-Wafer Interconnects in Silicon Substrates," Journal of Microelectromechanical Systems, 11:631-640, 2002.

Chui et al., "Independent detection of vertical and lateral forces with a sidewall-implanted dual-axis piezoresistive cantilever," Applied Physics Letters, 72:1388-1390, 1998.

Fernholz et al., "New developments and applications of skin-friction measuring techniques," Meas. Sci. Technol., 7:1396-1409, 1996.

Fourguette, D. et. al., "Miniature and MOEMS Flow Sensors," VioSense Corporation, 1-8, 2001.

Gabrielson, T., "Mechanical-Thermal Noise in Micromachined Acoustic and Vibration Sensors," IEEE Transactions on Electron Devices, 40:903-909, 1993.

Gad-El-Hak, M., "Flow Control: The Future," Journal of Aircraft, 38:402-418, 2001.

Gaitonde et al., "White Paper: Shock-Wave/Boundary Layer Interaction Research," May 16, 2002.

Gallas et al., "Lumped Element Modeling of Piezoelectric-Driven Synthetic Jet Actuators," AIAA Journal, 41:240-247, 2003.

Goldberg et al., "A Silicon Wafer-Bonding Technology for Microfabricated Shear-Stress Sensors with Backside Contacts." Solid State Sensor and Actuator Workshop, Hilton Head, SC, Jun. 13-16, 1994.

Greenblatt et al., "The control of flow separation by periodic excitation," Progress in Aerospace Sciences, 36:487-545, 2000.

Grigioni et al., "The Role of Wall Shear Stress in Unsteady Vascular Dynamics," Progress in Biomedical Research, 7: 204-212, 2002.

Harley et al., "High-sensitivity piezoresistive cantilevers under 1000 A thick," Applied Physics Letters, 75:289-291, Jul. 12, 1999.

Hefner et al., "An Overview of Concepts for Aircraft Drag Reduction," NASA Langley Research Center, 1977.

Ho et al., "Micro-Electro-Mechanical-Systems (MEMS) and Fluid Flows," Annu. Rev. Fluid Mech., 30:579-612, 1998.

Hyman, "Microfabricated Shear Stress Sensors, Part 2: Testing and Calibration," AIAA Journal, 37:73-78, 1999.

Kälvesten et al., "An integrated pressure-flow sensor for correlation measurements in turbulent gas flows," Sensors and Actuators A 52:51-58, 1996.

Kiesow, et al., "Modification of Near-Wall Structure in a Shear-Driven 3-D Turbulent Boundary Layer," Transactions of the ASME, 124:118-126, 2002.

Kimura, et al., "Measurements of wall shear stress of a turbulent boundary layer using a micro-shear-stress imaging chip," Fluid Dynamics Research, 24:329-342, 1999.

Ku, D., "Blood Flow in Arteries," Annu. Rev. Fluid Mech., 29:399-434, 1997.

Liu et al., "Surface Micromachined Thermal Shear Stress Sensor.".

Liu et al., "A Micromachined Flow Shear-Stress Sensor Based on Thermal Transfer Principles," Journal of Microelectromechanical Systems, 8: Mar., 1999.

Löfdahl et al., "MEMS-based pressure and shear stress sensors for turbulent flows," Meas. Sci. Technol., 10:665-686, 1999.

Naughton et al., "Modern developments in shear-stress measurement," Progress in Aerospace Science, 38:515-570, 2002.

Shajii et al., "A Microrfabricated Floating-Element Shear Stress Sensor Using Wafer-Bonding Technology," Journal of Microelectromechanical Systems, 1:89-94, Jun. 1992.

Padmanabhan et al., "A Wafer-Bonded Floating-Element Shear Stress Microsensor with Optical Position Sensing Photodiodes," Journal of Microelectromechanical Systems, 5:307-315, Dec., 1996.

Padmanabhan et al. "Micromachined Sensors for Static and Dynamic Shear-Stress Measurements in Aerodynamic Flows," 1997 International Conference on Solid-State Sensors and Actuators, Chicago, Jun. 16-19, 1997.

Pan et al., "Microfabricated Shear Stress Sensors, Part 1: Design and Fabrication," AIAA Journal, 37:66-72, Jan., 1999.

Papila et al., "Piezoresitive microphone design Pareto optimization: tradeoff between sensitivity and noise floor," 44th AIAA/ASME/ASCHE/AHS Structures, Structural Dynamics, and Materials Conference, Norfolk, VA, Apr. 7-10, 2003.

Partridge et al., "A High-Performance Planar Piezoresistive Accelerometer," Journal of Microelectromechanical Systems, 9:58-66, Mar., 2000.

Saini et al., "Scaling Relations for Piezoresistive Microphones," Proceedings of IMECE 2000: International Mechanical Engineering Congress and Exposition, Orlando, Florida, Nov. 5-10, 2000.

Schmidt et al., "Design and Calibration of a Microfabricated Floating-Element Shear-Stress Sensor," IEEE Transactions on Electron Device, 35:750-757, 1988.

Sheplak et al., "A Wafer-Bonded, Silicon-Nitride Membrane Microphone with Dielectrically-Isolated, Single-Crystal Silicon Piezoresistors," Solid-State Sensor and Actuator Workshop, Hilton Head, SC, Jun. 8-11, 1998.

Sheplak et al., "Dynamic Calibration of a Shear-Stress Sensor Using Stokes-Layer Excitation," AIAA Journal, 39: 819-823, May, 2001.

Sheplak et al., "Characterization of a Silicon-Micromachined Thermal Shear-Stress Sensor," AIAA Journal, 40:1099-1104, Jun., 2002.

Shyy et al., "Flapping and flexible wings for a biological and micro air vehicles," Progress in Aerospace Sciences, 35: 455-505, 1999.

Wang et al., "A Fully Integrated Shear Stress Sensor," To appear in the proceedings of Transducers '99, Sandai, Japan, 1999.

Winter, K.G., "An Outline of the Techniques Available for the Measurement of Skin Friction in Turbulent Boundary Layers," Prog. Aerospace Sci., 18:1-57, 1977.

Zhe et al., "A MEMS Device for Measurement of Skin Friction with Capacitive Sensing.".

* cited by examiner

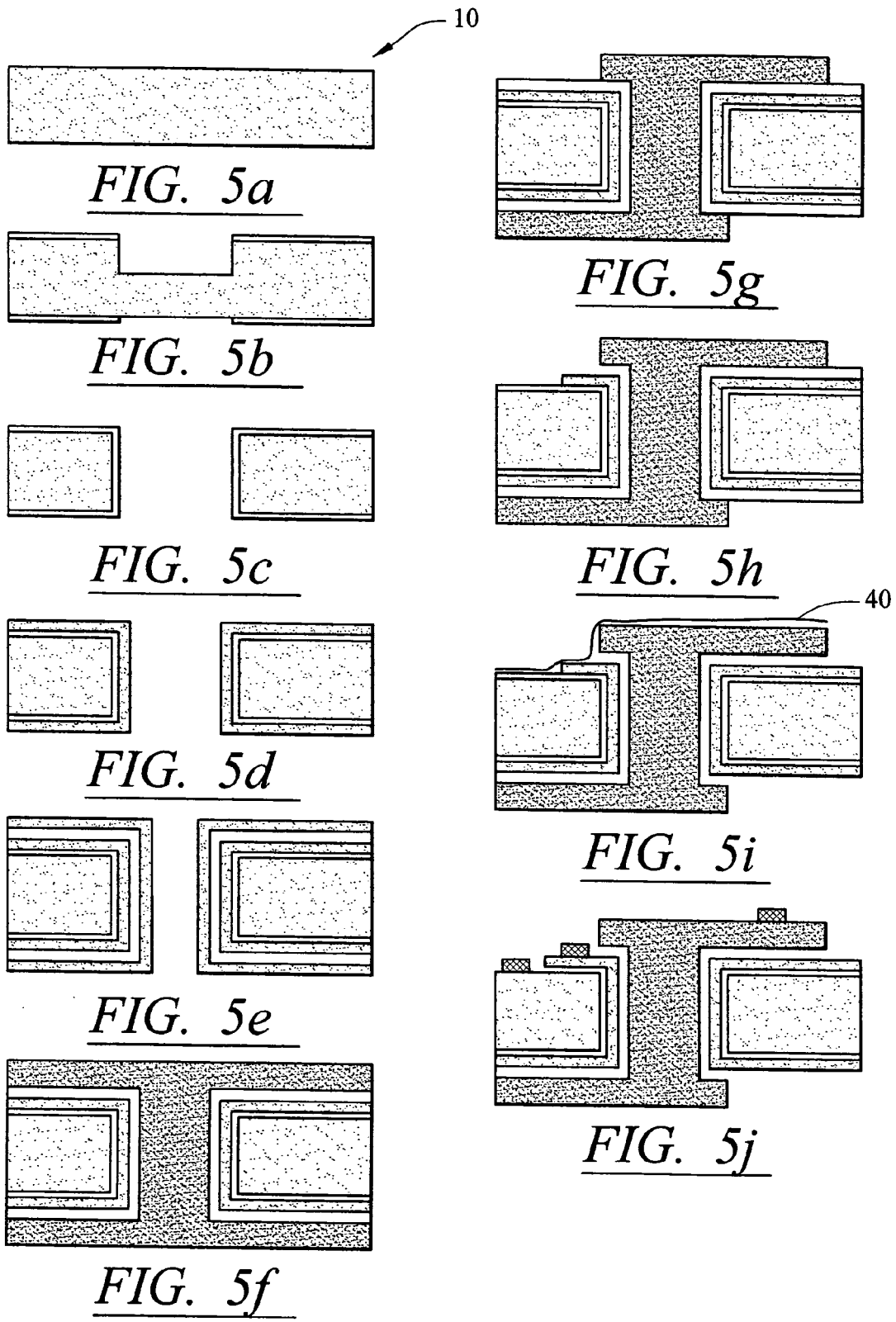

MICROELECTROMECHANICAL FLOATING ELEMENT FLOW SENSOR

FIELD OF THE INVENTION

This invention is directed generally to microelectromechanical systems (MEMS), and more particularly, to MEMS floating element flow sensors.

BACKGROUND

The measurement of mean and of fluctuating wall shear-stress in laminar, transitional, and turbulent boundary layers and channel flows has been used in industry and the scientific community. Measurement of mean shear-stress is related to the global state of fluid flow and may be used to determine the viscous skin-friction drag caused by the fluid on a body. The time-resolved, fluctuating shear-stress is a footprint of the turbulent processes responsible for the unsteady transfer of momentum to a body. Haritonidis, J. H. "The Measurement of Wall Shear Stress," Advances in Fluid Mechanics Measurements, Ed. by M. Gad-El-Hak, Springer-Verlag, 1989, pp. 229–261. Fluctuating shear-stress data can also provide physical insight into complex flow phenomena, including turbulent viscous drag, transition to turbulent flow, flow separation, and shock-wave/boundary layer interactions.

Accurate measurement of skin friction is of vital importance in numerous industries. For instance, skin friction drag forms approximately 50 percent of total vehicle drag for a typical subsonic transport aircraft. Hefner, J. N. and Bushnell, D. M., "An Overview of Concepts for Aircraft Drag Reduction," AGARD-R-654, 1977. As a result, accurate design of airfoils and other bodies requires accurate estimates of skin friction drag. Accurate measurement of wall shear-stress is vital for turbulence modeling and simulation validation as well as for the accurate assessment of skin friction drag reduction concepts. In supersonic flows, the measurement of wall shear-stress is critical to the understanding of shock-wave/boundary layer interactions which directly influence critical vehicle characteristics such as lift, drag, and propulsion efficiency. Gaitonde, D., Knight et al., "White Paper: Shock-Wave/Boundary Layer Interaction Research," AFOSR workshop on Shock-Wave/Boundary Layer Interactions organized by J. D. Schmisseur, May, 2002. In non-aerospace or hydrodynamic applications, the measurement of shear-stress can be used for industrial process control. Goldberg, H. D., Breuer, K. S. and Schmidt, M. A., "A Silicon Wafer-Bonding Technology for Microfabricated Shear-Stress Sensors with Backside Contacts," Technical Digest, Solid-State Sensor and Actuator Workshop, 1994, pp. 111–115. In biomedical applications, both mean and fluctuating wall shear-stress are important hemodynamic factors in the development of arterial pathologies, such as atherosclerosis. Grigoni, M., Daniele, C., D'Avenio, G. and Pontrelli, G. "The Role of Wall Shear Stress in Unsteady Vascular Dynamics," Progress in Biomedical Research, Vol. 7, No. 3, 2002, pp. 204–212.

Many different devices have been used to attempt to accurately determine shear-stress at walls susceptible to shear-stress from fluids flowing past the walls. For instance, clauser-plot techniques, preston tubes, obstacle methods, hot-film anemometers, mass-transfer probes, oil-film techniques, and liquid crystal methods have all been used; however, each with limited success. Winter, K. G., "An Outline of the Techniques Available for the Measurement of Skin Friction in Turbulent Boundary Layers," Progress in the Aeronautical Sciences, Vol. 18, 1977, pp. 1–57. It has been reported that uncertainties for mean shear-stress for surface fence methods, wall hot wires, wall pulsed wires, and oil-film are about 5 percent in incompressible flows and about 10 percent for supersonic flows. Naughton, J. W. and Sheplak, M. "Modern Developments in Shear Stress Measurement," Progress in Aerospace Sciences, Vol. 38, 2002, pp. 515–570. Accurate, direct measurement of fluctuating wall shear-stress has not been realized using conventional technologies.

Microelectromechanical systems (MEMS) are devices that operate on a very small scale, typically in a range of tens of microns to a few millimeters, and have been used to form shear-stress sensors. In some applications MEMS devices are imperceptible to the unaided human eye. MEMS devices mostly are fabricated using integrated circuits (IC) technology. MEMS devices include many different devices used for a variety of purposes. For instance, MEMS technology has been used to create shear-stress sensors; however, some MEMS shear-stress sensors have not achieved a desired level of performance of bandwidth, spatial resolution, stability, integration range, etcetera. For instance, thermal MEMS sensors have often not been accurate because of difficulty in obtaining unique calibration between heat transfer and wall shear-stress, measurement errors associated with mean temperature drift, and flow perturbations due to heat transfer to the flow.

In addition to these shear-stress sensing devices, MEMS floating element shear-stress sensors having been developed; however, the performance of these devices have suffered as well. For instance, a MEMS floating element sensor has been produced using a polyimide/aluminum surface micromachining process; however, the device was susceptible to moisture, which caused the mechanical properties of the device to change and caused mechanical sensitivity drift due to induced swelling. Schmidt, M. A., Howe, R. T., Senturia, S. D., and Haritonidis, J. H. "Design and Calibration of a Microfabricated Floating-Element Shear-stress Sensor," Transactions of Electron Devices, Vol. ED-35, 1988, pp. 750–757. In addition, air-dielectric interfaces subjected to charged species accumulation appeared as drift when detected by capacitive plates. Naughton, J. W. and Sheplak, M. "Modern Developments in Shear Stress Measurement," Progress in Aerospace Sciences, Vol. 38, 2002, pp. 519. Another floating element shear-stress sensor employed differential optical-shutter-based floating element sensors for turbulence measurements; however, the performance of this sensor suffers from front-side electrical contacts that interfere with fluid flow past the sensor and from remote mounting of the incident light source. Padmanabhan, A., Sheplak, M., Breuer, K. S., and Schmidt, M. A., "Micromachined Sensors for Static and Dynamic Sheer Stress Measurements in Aerodynamic Flows," Proc. Transducers 97, Chicago, Ill., 1997, pp. 137–140. A floating element shear-stress sensor employs a capacitive sensing scheme. In general, capacitive shear-stress sensors do not possess favorable scaling with shrinking size. Gabrielson, T., B., "Mechanical-thermal Noise in micromachined Acoustic and Vibration Sensors," IEEE Electron Devices, 40, 1993, pp. 903–909. Specifically, the electrical sensitivity is directly proportional to the electrode surface area, while the thermodynamic minimum detectable signal is inversely proportional to area. Gabrielson, 1993.

Other floating element shear-stress sensors have been developed; however, the performance of each device suffers as well. Thus, a need exists for a more accurate floating element shear-stress sensor.

SUMMARY OF THE INVENTION

This invention relates to a microelectromechanical shear-stress sensor, which may also be referred to as a flow rate sensor, usable to detect shear-stress found in surfaces of bodies across which a fluid, such as a gas or liquid flows and having one or more transduction mechanisms mounted normal to the direction of the force applied to the sensor. The microelectromechanical shear-stress sensor may be used to determine shear-stress along surfaces on an aircraft, in piping systems, on boat hulls, as a flow rate meter, and in innumerable other applications. The microelectromechanical shear-stress sensor may be installed so that the top surface of the floating element of the sensor is in, or substantially in, a plane that a surface in which a body to be tested resides. In other words, the top surface of the floating element may be mounted flush with an outside surface of a body, or an inside surface of a pipe wall. The microelectromechanical shear-stress sensor may use electrical contacts extending from a backside of the sensor, thus leaving a protrusion free top surface across which a fluid may flow.

The microelectromechanical shear-stress sensor may include, in at least one embodiment, a floating element having a top surface residing in a plane. The floating element may be supported so that a bottom surface of the floating element does not support the floating element from below using one or more arms extending from each corner of the floating element for supporting the at least one floating element. The arms may include at least one side surface for locating a transduction mechanism normal to the shear force applied to the top surface of the floating element. In at least one embodiment, the side surface for locating a transduction mechanism may be positioned generally orthogonal to the top surface of the floating element.

The microelectromechanical shear-stress sensor may also include at least one transduction mechanism coupled to the at least one arm and positioned generally orthogonal to the plane of the top surface. The transduction mechanism may be, but is not limited to being, a piezoresistor. In one embodiment, the microelectromechanical shear-stress sensor may include at least four transduction mechanisms forming a Wheatstone bridge. Contacts in the plane of the top surface of the floating element may be used to connect the transduction mechanisms to each other. In addition, the transduction mechanisms may be coupled together using electronic through wafer interconnects extending away from the top surface of floating element through one or more vias in a support wafer. In at least one embodiment, the contacts may extend towards a bottom surface of the floating element and generally orthogonal to a top surface of the floating element.

The microelectromechanical shear-stress sensor may also include a coating on the floating element for protecting sensor gaps from debris. The microelectromechanical shear-stress sensor may also include a temperature compensation system. In at least one embodiment, the temperature compensation system may be formed from a plurality of transduction mechanisms forming at least two Wheatstone bridges. A first Wheatstone bridge may be coupled to the floating element, and a second Wheatstone bridge may be coupled to rigid portions of the surface proximate to the surface surrounding the microelectromechanical shear-stress sensor. The response detected in the second Wheatstone bridge is shear-stress independent but both bridges are equally sensitive to temperature. The difference between the first and second Wheatstone bridges is a temperature compensated output that eliminates zero shear-stress offset voltage due to transduction mechanism mismatch.

At least one advantage of the microelectromechanical shear-stress sensor is that the piezoresistive transduction scheme of this invention is less expensive to develop, simpler to fabricate, and more robust than conventional capacitive devices.

Another advantage of this invention is the top surface used to identify shear-stress does not include any protrusions that could disrupt fluid flow across the floating element and thereby affect the microelectromechanical shear-stress sensors ability to record accurate data.

Yet another advantage of this invention is that by orienting the transduction mechanisms normal to the direction of force applied to the top surface of the floating element, the performance of the floating elements is enhanced because the sensor measures bending loading rather than axial loading.

Still another advantage of this invention is that orienting the transduction mechanisms normal to the direction of force applied to the top surface of the floating element, the transverse acceleration stress is more accurately measured.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

FIGS. 5a–5j depict the fabrication process of the wafer forming the microelectromechanical shear stress sensor.

DETAILED DESCRIPTION OF THE INVENTION

Figure 1:
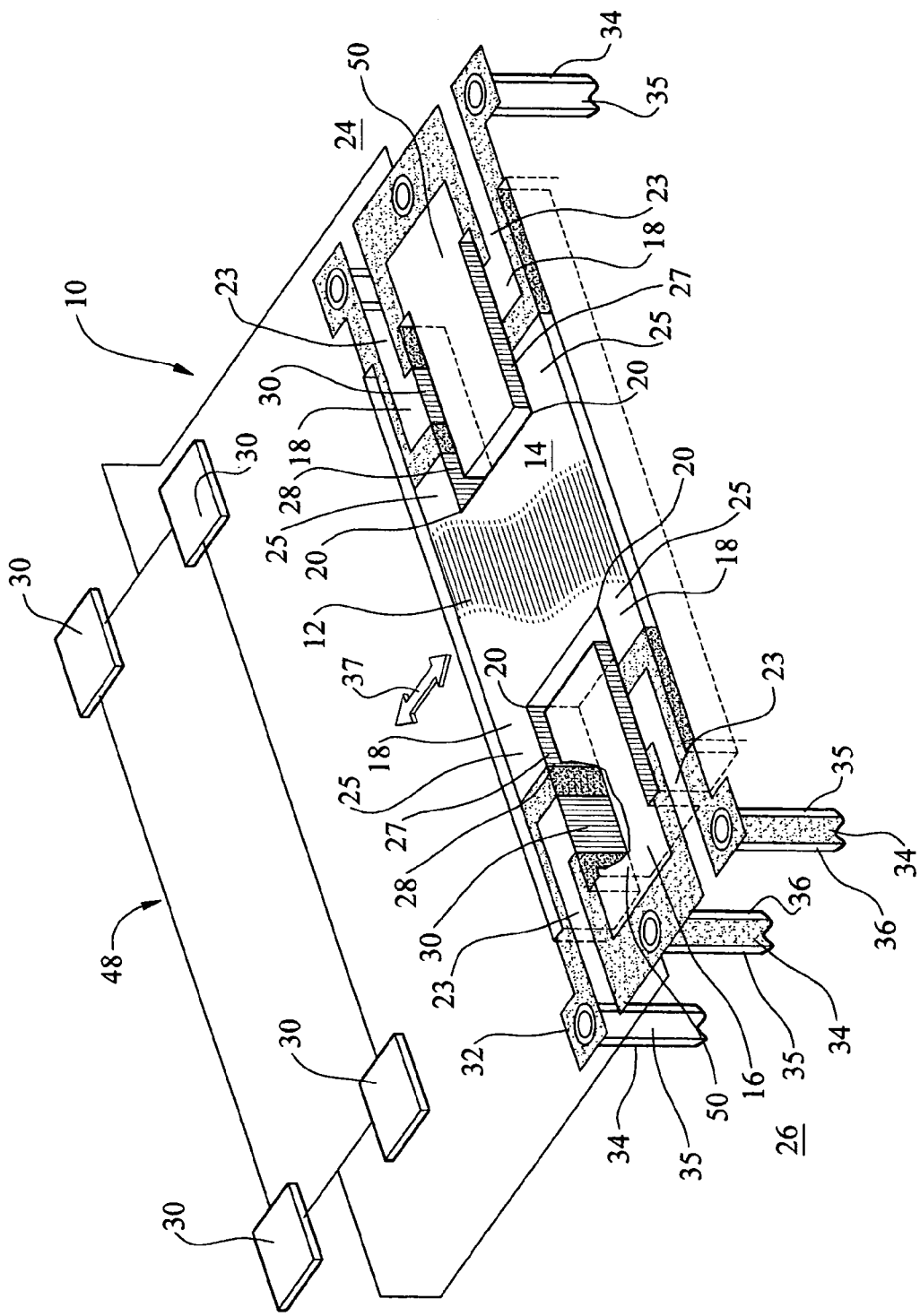
FIG. 1 is a perspective view of a floating element shear-stress sensor including at least some of the aspects of this invention.

As shown in FIGS. 1–5j, this invention is directed to a microelectromechanical shear-stress sensor 10, which may also be referred to as a flow rate sensor, for measuring shear-stress caused by surface friction induced by a fluid flowing past a surface of a body. In at least one embodiment, the microelectromechanical shear-stress sensor 10 includes a sensing surface capable of being flush mounted, and the sensing surface may not include any protrusions, such as electrical connectors, that can interfere with fluid flow past the sensing surface. The microelectromechanical shear-stress sensor 10 may also include one or more transduction mechanisms mounted to one or more arms connected to the floating element generally normal to forces applied to the sensor 10.

As shown in FIGS. 1–4, the microelectromechanical shear-stress sensor 10 may be formed from one or more floating elements 12 having a top surface 14 residing in a plane 16. In at least one embodiment, the floating element 12 may be about 100 $\mu$m in width, about 100 $\mu$m in length, and about 1 $\mu$m in depth. However, in other embodiments, the floating element 12 is not limited to these dimensions. The floating element 12 may be formed from one or more layers.

In at least one embodiment, the floating element 12 may be formed from silicon or other appropriate materials.

Figure 4:
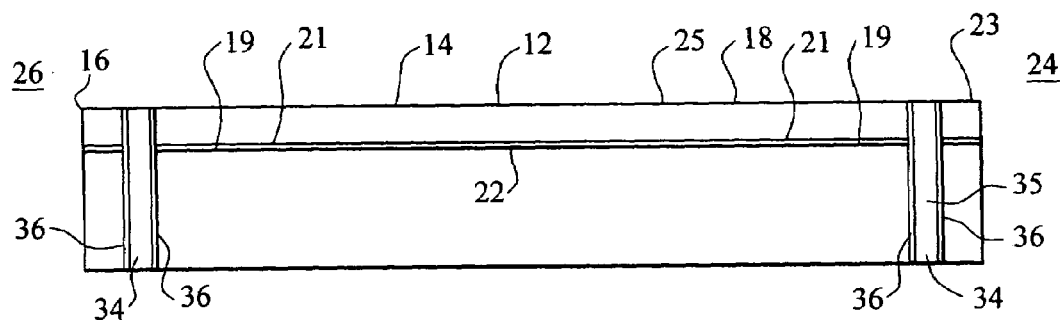
FIG. 4 is a cross-sectional view of the embodiment of this invention taken at 4—4 in FIG. 2.

The floating element 12 may be supported by at least one arm 18, which may also be referred to as a tether, extending from each corner 20 of the floating element 12. The arm 18 may suspend the floating element 12 so that a bottom surface 22 of the floating element 12 does not support the floating element 12. In at least one embodiment, as shown in FIG. 4, the arm 18 may include a layer 19 coupled to a bottom surface 21 of the arm 18. The layer 19 may at least be coupled to a portion of the arm at a first end 23 of the arm 18 opposite to a second end 25 of the arm 18 coupled to the floating element 12. The layer may be, but is not limited to, silicon dioxide. In at least one embodiment, the arm 18 may be about 2 $\mu$m in width, about 300 $\mu$m in length, and about 1 $\mu$m in depth. The arm 18 may be spaced apart from an adjacent wafer forming a gap 27 of about 1 $\mu$m in width. The dimension of the gap 27 may vary between about 0.1 micrometers ($\mu$m) and about 100 $\mu$m in other embodiments.

Figure 2:
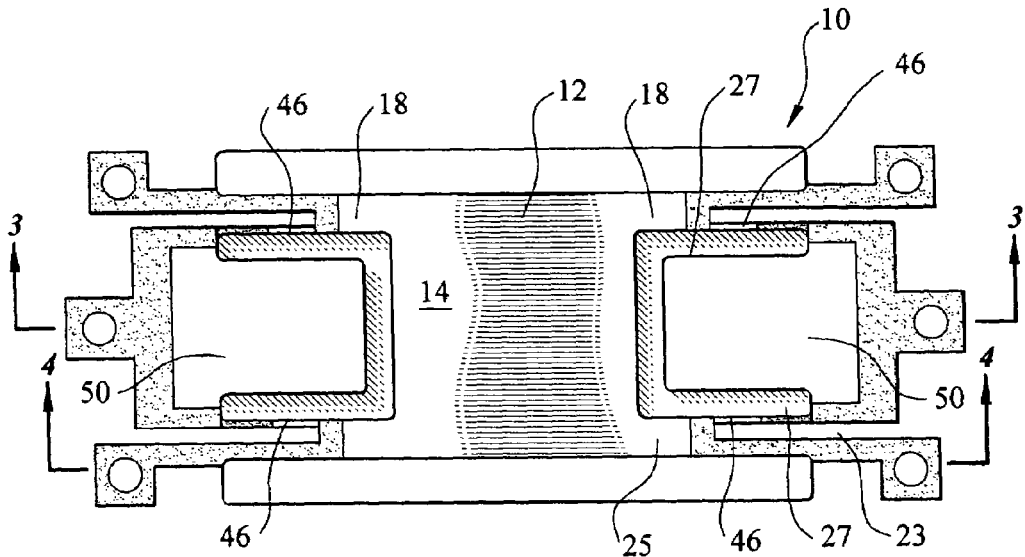
FIG. 2 is a top view of an embodiment of this invention.
Figure 3:
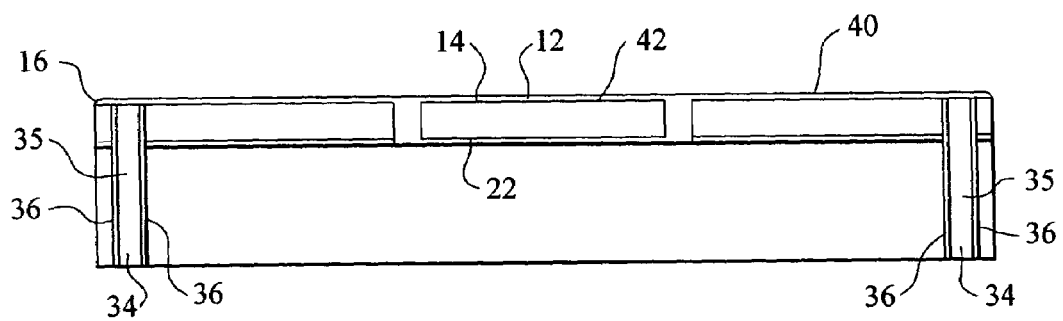
FIG. 3 is a cross-sectional view of the embodiment of this invention taken at 3—3 in FIG. 2.

In at least one embodiment, the microelectromechanical shear-stress sensor 10 may include four arms 18, as shown in FIGS. 1–3, extending from the corners 20 of the floating element 12. Two of the arms 18 may be generally parallel to each other and may extend from the floating element 12 in a first direction 24. The other two arms 18 may be generally parallel to the each other and may extend from the floating element 12 in a second direction 26 generally opposite to the first direction 24.

The arm 18 may include at least one side surface 28 having a portion capable of positioning a transduction mechanism 30 generally normal to a force to be applied to the top surface 14 of the floating element 12. The force may be applied generally parallel to the top surface 14, as indicated by arrow 37 in FIG. 1. In at least one embodiment, the side surface 28 may have a portion that is generally orthogonal to the at least one plane 16 in which the top surface 14 resides. The side surface 28 may be sized sufficiently to accommodate at least one transduction mechanism 30. The transduction mechanism 30 may be capable of sensing shear-stress created in the arms 18 supporting the floating element 18 and transmitting signals to a processor. In at least one embodiment, the transduction mechanism 30 may be a p-type piezoresistive silicon strain gauge mechanism. In other embodiments, the transduction mechanism 30 may be formed from other transduction mechanisms, such as, but not limited to, a capacitor system, or other appropriate mechanism. The piezoresistive transduction mechanism 30 may be, but is not limited to, being capable of identifying stresses having magnitudes of about 1 milliPascal and about 999 kiloPascals.

In at least one embodiment, the microelectromechanical shear-stress sensor 10 may include at least four transduction mechanisms 30. In this embodiment, one transduction mechanism 30 may be coupled to a side surface 28 on each of fours arms 18 and electrically coupled together to form a conventional Wheatstone bridge. The transduction mechanisms 30 may be coupled together using contacts 32, which may reside generally in the plane 16 in which the top surface 14 of the floating element 12 resides. In at least one embodiment, the contacts 32 may be formed from aluminum or other conductive materials. In embodiments having transduction mechanisms 30 coupled together in a Wheatstone bridge formation, transduction mechanisms 30 coupled to two arms 18 parallel to each other and extending from the floating element 12 in a first direction 24 may be coupled to transduction mechanisms 30 coupled to two arms 18 parallel to each other and extending from the floating element 12 in a second direction 26 using a plurality of contacts 34 extending through one or more vias 35 in a support wafer 50 in a direction away from the top surface 14 of the floating element 12.

In at least one embodiment, the plurality of contacts 34, which may be referred to as electronic through-wafer interconnects (ETWI), may extend generally orthogonal to the top surface 14 of the at least one floating element 12 and toward the bottom surface 22. The vias 35 may have a generally cylindrical cross-section and a generally constant diameter throughout its length. The plurality of contacts 34 may be formed from a polysilicon through wafer interconnect housed in an insulation layer 36, which may be formed from one or more vias 35 in the support wafer 50. As shown in FIG. 4, the vias 35 may be formed by using plasma anisotropic etching with fill, deep-reactive ion etching or other appropriate processes, some of which are described in "Process Compatible Polysilicon-Based Electrical Through-Wafer Interconnects in Silicon Substrates," Chow et al., Journal of Microelectromechanical Systems, Vol. 11, No. 6, December, 2002. The insulation layer 36 may be, but is not limited to silicon dioxide. The plurality of contacts 34 may be formed by backfilling a through-wafer vias 35 in the floating element 12 with an in situ-doped polycrystalline silicon.

The microelectromechanical shear-stress sensor 10 may also include a silicon nitride hydrophobic passivation layer 40 that may improve the transduction mechanism stability by reducing the surface potential drift and may waterproof the transduction mechanism 30. The silicon nitride hydrophobic passivation layer 40 may be located on a top surface of the microelectromechanical shear-stress sensor 10. The microelectromechanical shear-stress sensor 10 may also include a coating 42 on at least a portion of the top surface 14 of the floating element 12. The coating 42 may be placed on the top surface 14 to protect sensor gaps from debris. The coating 42 may be may be formed from a polymer, such as, but not limited to, parylene, or other appropriate materials.

The microelectromechanical shear-stress sensor 10 may also include a temperature compensation system 44. In at least one embodiment, the temperature compensation system 44 may be composed of at least two Wheatstone bridges. A first Wheatstone bridge assembly 46 may be located on the floating element 12 and a second Wheatstone bridge assembly 48 may be located on a surface proximate to a support wafer 50. Thus, the response recorded by the second Wheatstone bridge 48 is shear-stress independent but displays the same temperature sensitivity as the first Wheatstone bridge assembly 46. The difference between the output from the first Wheatstone bridge assembly 46 and the output from the second Wheatstone bridge assembly 48 provides a temperature compensated output that also may eliminate zero shear-stress offset voltage that may result from transduction mechanism 30 mismatch.

The microelectromechanical shear-stress sensor 10 may be formed using a fabrication process developed for a thermoelastically actuated ultrasonic resonator possessing electronic through-wafer interconnects. The fabrication process may begin, as shown in FIG. 5a, by thermally oxidizing a wafer and an oxide gap where the suspended microstructure will reside, is formed on a frontside of the wafer. The wafer may be coated with silicon nitride and the backside may be patterned and etched to expose regions forming vias 35. Vias 35 may be etched into the sensor 10 to approximately a midpoint of the sensor 10, as shown in FIG. 5b, using anisotropic silicon etching (KOH:H$_2$O). The sensor 10 may be flipped and holes may be etched into the backside of the sensor 10 and may meet with the holes in the frontside, thereby forming a hole completely through the sensor 10, as shown in FIG. 5c. Oxide and polysilicon may be deposited and doped, as shown in FIG. 5d. Oxide and then polysilicon may be deposited again to form a shield, as shown in FIG. 5e. Additional polysilicon may be added to fill the hole, as shown in FIG. 5f. The polysilicon may be patterned, as shown in FIGS. 5g and 5h. A passivation layer 40 is deposited, as shown in FIG. 5i, and the contact vias 35 may be etched with a polysilicon mask and metal pads may be formed, as shown in FIG. 5j.

The microelectromechanical shear-stress sensor 10 may be installed on a surface of a body having a fluid, such as a liquid or a gas, flowing past the body. The microelectromechanical shear-stress sensor 10 may be used to determine shear-stress along surfaces on an aircraft, in piping systems, on boat hulls, and in innumerable other applications. The microelectromechanical shear-stress sensor 10 may be installed so that the top surface 14 of the floating element 16 is in, or substantially in, a plane that a surface in which a body to be tested resides. As a fluid passes the microelectromechanical shear-stress sensor 10, a force, as shown by the arrow 37 in FIG. 1, produced by the wall shear-stress on the floating element causes the arms 18 to deform, which creates a mechanical stress field in the arms 18. In embodiments where the transduction mechanism 30 is a piezoresistor, the transduction mechanism 30 responds to the mechanical stress field with a change in resistance from its nominal unstressed value. The conversion of the shear-stress induced resistance charge into an electrical voltage change necessitates a bias current, which may be between about 1 and about 10 milliamps, flowing through the transduction mechanism 30. The bias current may be driven by a constant current source, a constant voltage source, or other source. The shear-stress that develops in the arms 18 may be detected by the transduction mechanisms and sent to a processor for storage, comparison, or other uses.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A microelectromechanical flow rate sensor, comprising:
at least one floating element having a top surface residing in a plane;
at least one arm extending from each corner of the floating element for supporting the at least one floating element, wherein the at least one arm includes at least one side surface that is generally normal to an average direction of fluid flow past the top surface of the at least one floating element;
at least one transduction mechanism coupled to the at least one arm and positioned generally normal to an average direction of fluid flow past the top surface of the at least one floating element.

2. The microelectromechanical flow rate sensor of claim 1, wherein the at least one transduction mechanism is a piezoresistor shear-stress transduction mechanism.

3. The microelectromechanical flow rate sensor of claim 1, wherein the at least one arm comprises four arms, each arm extending from a different corner of the at least one floating element, wherein two of the arms are generally parallel to each other and extend from the at least one floating element in a first direction and two other arms are generally parallel to each other and extend from the at least one floating element in a second direction generally opposite to the first direction.

4. The microelectromechanical flow rate sensor of claim 3, wherein at least one transduction mechanism is coupled to each of the four arms.

5. The microelectromechanical flow rate sensor of claim 4, wherein the transduction mechanisms are coupled together to form a Wheatstone bridge.

6. The microelectromechanical flow rate sensor of claim 5, wherein the transduction mechanisms are coupled together using electronic through wafer interconnects in the plane in which the top surface of the at least one floating element resides and a plurality of electronic through wafer interconnects extending generally orthogonal to the top surface of the at least one floating element and toward a bottom surface of the at least one floating element, thereby providing a non-obstructed top surface.

7. The microelectromechanical flow rate sensor of claim 6, wherein the electronic through wafer interconnects in the plane in which the top surface of the at least one floating element resides are formed from aluminum.

8. The microelectromechanical flow rate sensor of claim 6, wherein the plurality of electronic through wafer interconnects extending generally orthogonal to the top surface of the at least one floating element and toward a bottom surface of the at least one floating element are formed from a polysilicon through wafer interconnect housed in an insulation layer.

9. The microelectromechanical flow rate sensor of claim 8, wherein the insulation layer comprises silicon dioxide.

10. The microelectromechanical flow rate sensor of claim 8, wherein at least one electronic through wafer interconnect is formed by back filling a through-wafer vias through the at least one floating element with an in situ-doped polycrystalline silicon.

11. The microelectromechanical flow rate sensor of claim 8, wherein the through-wafer trench may be formed using deep-reactive ion etching.

12. The microelectromechanical flow rate sensor of claim 1, wherein the at least one floating element is formed from silicon.

13. The microelectromechanical flow rate sensor of claim 1, further comprising a layer coupled to a portion of a bottom surface of the at least one arm at an end of the at least one arm opposite to the end of the arm coupled to the at least one floating element for suspending the floating element.

14. The microelectromechanical flow rate sensor of claim 13, wherein the layer is comprised of silicon dioxide.

15. The microelectromechanical flow rate sensor of claim 1, further comprising at least one contact coupled to a first side of the transduction mechanism and extending generally orthogonal to the top surface of the at least one floating element and toward a bottom surface of the at least one floating element.

16. The microelectromechanical flow rate sensor of claim 13, further comprising at least one coating comprising a silicon nitride hydrophobic passivation layer.

17. The microelectromechanical flow rate sensor of claim 13, further comprising at least one coating on at least the top surface of the floating element.

18. The microelectromechanical flow rate sensor of claim 17, wherein the coating comprises a polymer.

19. The microelectromechanical flow rate sensor of claim 18, wherein the polymer comprises parylene.

20. The microelectromechanical flow rate sensor of claim 1, further comprising a temperature compensation system.

21. The microelectromechanical flow rate sensor of claim 20, wherein the temperature compensation system comprises a plurality of transduction mechanisms forming a Wheatstone bridge.

22. A microelectromechanical flow rate sensor, comprising:
   at least one floating element having a top surface residing in a plane and at least four corners;
   at least one arm extending from each of four corners of the floating element for supporting the at least one floating element, wherein each arm extends from a different corner of the at least one floating element, wherein two of the arms are generally parallel to each other and extend from the at least one floating element in a first direction and two other arms are generally parallel to each other and extend from the at least one floating element in a second direction generally opposite to the first direction;
   at least one piezoresistor strain gauge transduction mechanism coupled to each of the arms and positioned generally normal to an average direction of fluid flow past the top surface of the at least one floating element.

23. The microelectromechanical flow rate sensor of claim 22, wherein the transduction mechanisms are coupled together to form a Wheatstone bridge.

24. The microelectromechanical flow rate sensor of claim 23, wherein the transduction mechanisms are coupled together using contacts in the plane in which the top surface of the at least one floating element resides and a plurality of electronic through wafer interconnects extending generally orthogonal to the top surface of the at least one floating element and toward a bottom surface of the at least one floating element, thereby providing a non-obstructed top surface.

25. The microelectromechanical flow rate sensor of claim 24, wherein the contacts in the plane in which the top surface of the at least one floating element resides are formed from aluminum.

26. The microelectromechanical flow rate sensor of claim 22, wherein the plurality of electronic through wafer interconnects extending generally orthogonal to the top surface of the at least one floating element and toward a bottom surface of the at least one floating element are formed from a polysilicon through wafer interconnect housed in a silicon dioxide insulation layer.

27. The microelectromechanical flow rate sensor of claim 24, wherein at least one contact is formed by back-filling a through-wafer trench through the at least one floating element with an in-situ-doped polycrystalline silicon.

28. The microelectromechanical flow rate sensor of claim 24, wherein the through-wafer trench may be formed using deep-reactive ion etching.

29. The microelectromechanical flow rate sensor of claim 22, wherein the at least one floating element is formed from silicon.

30. The microelectromechanical flow rate sensor of claim 22, further comprising a layer coupled to a portion of a bottom surface of the at least one arm at an end of the at least one arm opposite to the end of the arm coupled to the at least one floating element for suspending the floating element.

31. The microelectromechanical flow rate sensor of claim 30, wherein the layer is comprised of silicon dioxide.

32. The microelectromechanical flow rate sensor of claim 22, further comprising at least one contact coupled to a first side of the transduction mechanism and extending generally orthogonal to the top surface of the at least one floating element and toward a bottom surface of the at least one floating element.

33. The microelectromechanical flow rate sensor of claim 22, further comprising at least one coating on at least the top surface of the floating element.

34. The microelectromechanical flow rate sensor of claim 33, wherein the coating comprises a silicon nitride hydrophobic passivation layer.

35. The microelectromechanical flow rate sensor of claim 33, wherein the coating comprises a polymer.

36. The microelectromechanical flow rate sensor of claim 35, wherein the polymer comprises parylene.

37. The microelectromechanical flow rate sensor of claim 22, further comprising a temperature compensation system comprising a plurality of transduction mechanisms forming a Wheatstone bridge.

* * * * *